United States Patent [19]

Barnett et al.

[11] Patent Number: 4,999,198

[45] Date of Patent: Mar. 12, 1991

[54] POLYAPHRONS AS A DRUG DELIVERY SYSTEM

[75] Inventors: Stanley M. Barnett; Joan M. Lausier, both of Wakefield; Samuel J. Montalto, Westerly, all of R.I.

[73] Assignee: The Board of Governors for Higher Education, State of Rhode Island and Providence Plantations, Providence, R.I.

[21] Appl. No.: 512,043

[22] Filed: Apr. 17, 1990

Related U.S. Application Data

[63] Continuation of Ser. No. 328,801, Mar. 23, 1989, abandoned, which is a continuation of Ser. No. 939,548, Dec. 9, 1986, abandoned, which is a continuation of Ser. No. 603,455, Apr. 24, 1984, abandoned.

[51] Int. Cl.⁵ .......................... A61K 9/58; A61K 9/22
[52] U.S. Cl. ................................... 424/449; 424/462; 604/890.1
[58] Field of Search ........... 428/402.2, 402.22, 402.21; 264/4, 4.1, 4.3, 4.32, 4.33, 4.4, 4.6, 4.7; 222/1; 260/705–708; 424/449, 455, 450, 461, 462, 479, 481, 482; 604/890.1

[56] References Cited

U.S. PATENT DOCUMENTS 3,921,636  11/1975  Zaffaroni ........................ 604/890

OTHER PUBLICATIONS

"Separations Using Collodial Gas Aphrons", Sebba et al., paper presented at the 2nd International Congress on Chemical Engineering, Oct. 1981.

Primary Examiner—Thomas Wallen
Attorney, Agent, or Firm—Samuels, Gauthier & Stevens

[57] ABSTRACT

A polyaphron is formed having a continuous phase and a disperse phase. A drug is carried in the dispersed phase. The polyaphron is placed in contact with a medium and the drug is transferred from the disperse phase into the medium.

15 Claims, 3 Drawing Sheets

4,999,198

POLYAPHRONS AS A DRUG DELIVERY SYSTEM

This is a continuation of co-pending application Ser. No. 328,801 filed on Mar. 23, 1989 now abandoned, which is a continuation of co-pending application Ser. No. 939,548 filed on Dec. 9, 1986 now abandoned, which is a continuation of application Ser. No. 603,455, filed on Apr. 24, 1984 now abandoned.

BACKGROUND OF THE INVENTION

The cost of introducing new chemical entities into systems has led many companies to search for alternative methods of drug administration. In the 1980s, a new class of drug dosage forms was developed to provide controlled topical administration of a drug at a predetermined rate. S. K. Chandrasekaran, J. E. Shaw in *Control and Release of Bioactive Materials*, (R. W. Baker, ed.) Academic Press, Inc., New York, 1980, p. 99. The present invention in the preferred embodiment is devoted to a novel drug delivery system.

Polyaphrons, as defined herein, are multi-phase systems. Basically, they consist of a disperse of suspended phase such as tiny droplets of between about 1 $\mu$m to 1 mm encased in a continuous phase.

Where an oil is used as the dispersed phase and water is the continuous phase (immiscible liquids), it has been discovered that a therapeutically active substance such as a plant growth regulator or drug may be dissolved in an acceptable carrier such as oil. The polyaphron is then placed in communication with a medium and the substance can be slowly released into the medium. Preferably, the release is the substance leaving the disperse phase and entering the medium. Alternatively, the disperse phase can migrate into the medium and the substance released or a combination of both. Such a medium could be the plant in a soil or hydrophonic system of another organism such as the human body. For topical applications, the aphron could be gelled by carrying out a solvent or suspension-type polymerization in the oil phase forming something similar to a "bandaid" for long-term and steady delivery of drugs (the substance).

Polyaphrons or biliquid foams are preferably created when the gas phase in a colloidal gas aphron is replaced by an immiscible liquid.

The invention broadly comprises forming a polyaphron, the polyaphron comprising at least two fluid phases; a first continuous phase and a second disperse phase. The dispersed phase carries a substance which can be transferred to another medium.

DESCRIPTION OF THE PREFERRED EMBODIMENT

Figure 1:
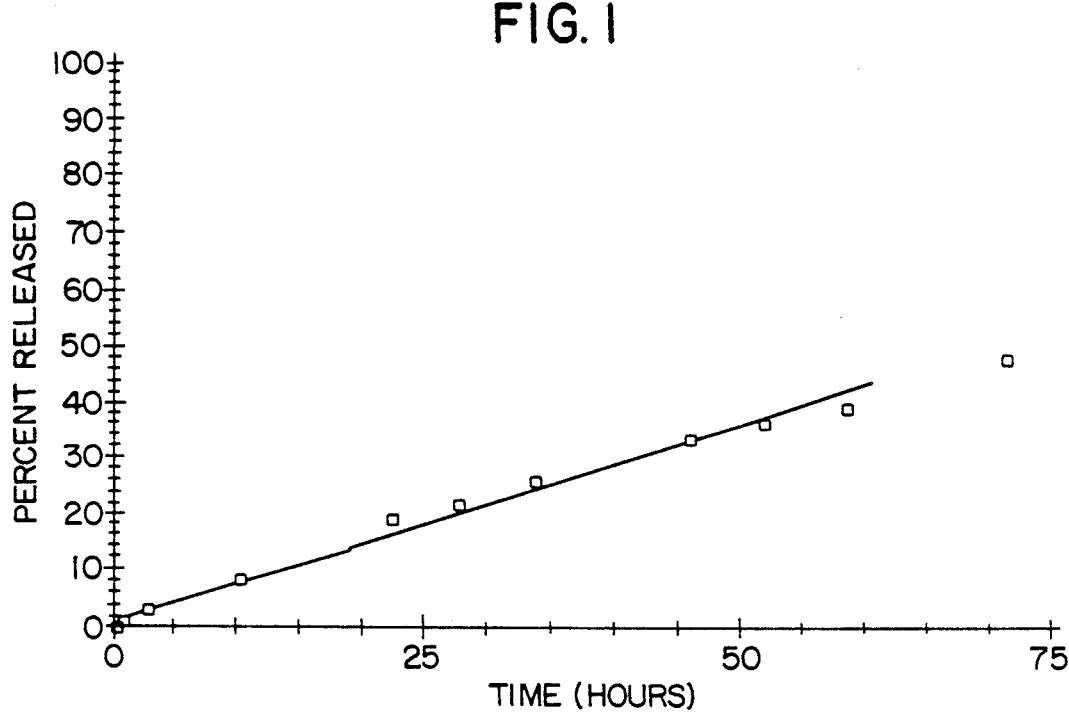
FIGS. 1–6 are graphical representations of the results of the polyaphron systems.

The invention will be described in reference to a polyaphron wherein water is the continuous phase and certain selected "oils" are the disperse or suspended phase. In the preferred embodiment the oil (or disperse phase) is usually present in the amounts exceeding 80% so that the system behaves like a gel. Surface active agents including water soluble and oil soluble surfactants may be used and the phases may be reversed. Further, any system with immiscible liquids may be used where the substance to be delivered is be carried in one of the phases whether suspended, dissolved, etc.

Ingredient suitability for a polyaphron was evaluated by determining the solubility of scopolamine in a series of oils, followed by manufacture of polyaphrons with each oil to test for physical stability. To this end, scopolamine free base was prepared by reacting 500 mg of the hydrobromide salt with 10 ml of 1% sodium bicarbonate solution. The free base formed was extracted with chloroform, and the solvent was evaporated by air. Prior to use, the purity of the free base was verified by HPLC. The free base appeared as a clear viscous liquid.

100 ml volumes of commercially availably mineral, almond, peanut, corn, and sesame oils were placed in separate beakers and heated to approximately 50° C. while being gently stirred. Approximately 100 mg of free base, weighed on a glass slide, was introduced into the warm oil. Within twenty minutes the scopolamine base was dissolved in all the oils except mineral oil. When the mineral oil containing the scopolamine was cooled with agitation, a fine dispersion of the drug resulted. This dispersion was also considered suitable for a polyaphron system.

Polyaphron systems were prepared using each of the oils in order to determine the most stable formulation. A solution containing 2000 ppm of sodium lauryl sulfate in water was used to produce a form in a foam generator such as a venturi, cyclone or other high shear device for introducing a gas into a liquid. The gas phase of the foam was gradually replaced with 100 ml of drug-charged oil containing 1 drop of Tergitol 15-S surfactant by slowing adding the oil to 5 ml of foam with stirring. When 1 ml of foam was used, it was possible to make polyaphrons with all of the oils. However, the systems were not appreciably stable for any significant period of time, with the exception of the peanut and mineral oils. When 5 ml of foam was used, all systems were initially stable, with the mineral and peanut oil systems proving superior in this regard. Systems prepared at this level of foam were thicker and lighter in color, indicating a finer dispersion. As a result of these trials, mineral and peanut oil polyaphron systems were selected for release trails.

Release studies of the peanut and mineral oil systems were performed using 150 mg of scopolamine free base in 100 ml of oil containing 1 drop of Tergitol 15-S surfactant and 5 ml of foam to form a polyaphron.

Approximately 40 ml of each polyaphron was partitioned against 100 ml of distilled water at 37° C. In a container, the 100 ml of water formed a lower layer and the aphron formed an upper layer, the layers separated by the water/polyaphron interface. A stainless steel sampling needle was attached to container so samples could be drawn from the water. A small magnetic stirrer inserted into the foam was used to insure uniform dispersion of any scopolamine released from the polyaphron into the water. The stirring rate was such as not to disturb the polyaphron/water interface.

Analysis of the drug released into distilled water was completed by reverse-phase high performance liquid chromatography, using a Bondapak $C_{18}$ column. The mobile phase consisted of a 30% acetonitrile on water solution, with PIC Reagent $B_7$ added. The chromatographic conditions were: flow rate 1.6 ml/min, wavelength 254 nm, chart speed 30 cm/hr, and sensitivity at 0.05 AUFS.

The instability of the polyaphrons when made with almond, corn, and sesame oil could be attributed to the presence of fatty acids due to oxidation of the oils. This may have been responsible for the neutralization of the surfactants thus destroying some of the foam. Also, the affinity of different oils for surfactants in the foam may have affected the integrity of the interface.

The release of scopolamine was considered a preliminary study to detect any release of drug from the polyaphron. The concern with absolute release rates was not initially considered. With the peanut oil polyaphron, no detectable release of scopolamine was observed after 68 hours. Since the scopolamine had an appreciable solubility in this oil, it didn't partition to any extent with water. The possibility exists that increasing the concentration of drug may provide a sufficient driving force to produce drug release. Apparently peanut oil is unsatisfactory for this drug system. The mineral oil polyaphrons showed a significant release of scopolamine after 48 hours. Due to a sampling error the 24 hour sample had to be discarded.

One problem experienced with the polyaphrons was that over a period of time, particularly at 37° C. there was some coalescense of oil at the air/polyaphron interface. This was expected but once the entire polyaphron layer was covered with a layer of mineral oil, no further break-down occurred. Since polyaphrons, like other dispersed systems, are subject to interfacial instabilities, it is felt that polymerization of the polyaphrons may significantly increase the life of the system. Further, polymerization would provide a more rigid polyaphron system, which would be more suitable for a transdermal delivery system.

Figure 2:
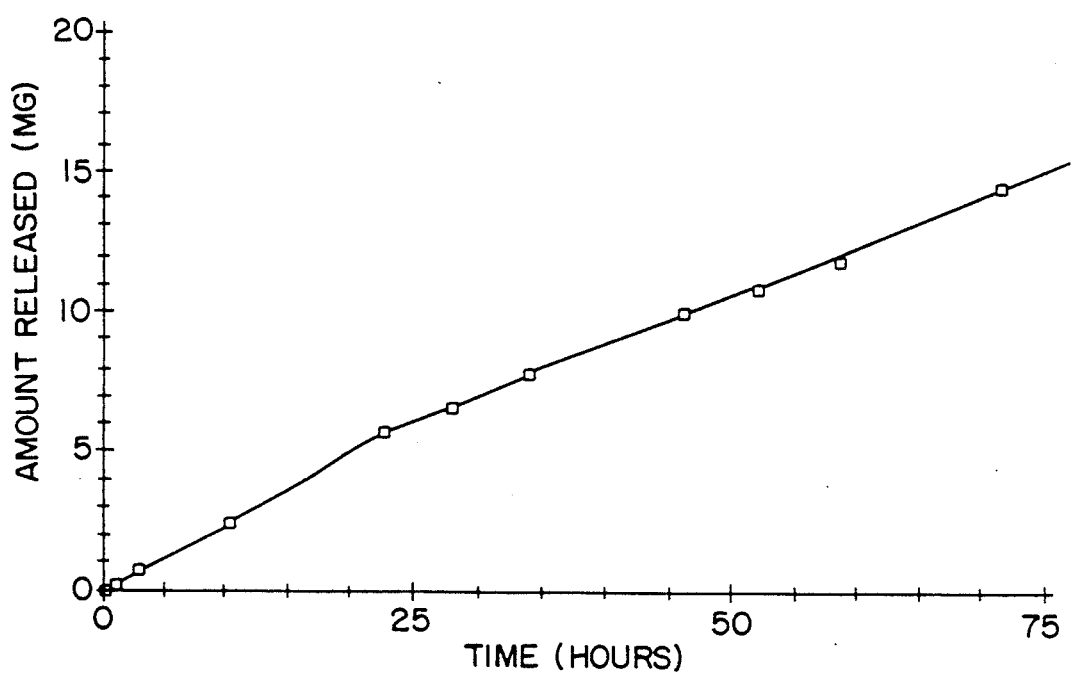

Further work was conducted with the polyaphron systems and the substance or drug scopolamine. The polyaphrons were created and the tests conducted as previously described. In two consecutive tests conducted using the mineral oil water polyaphron the drug scopolamine was released from the polyaphron at a constant rate of delivery for three days. See FIGS. 1 and 2.

Figure 3:
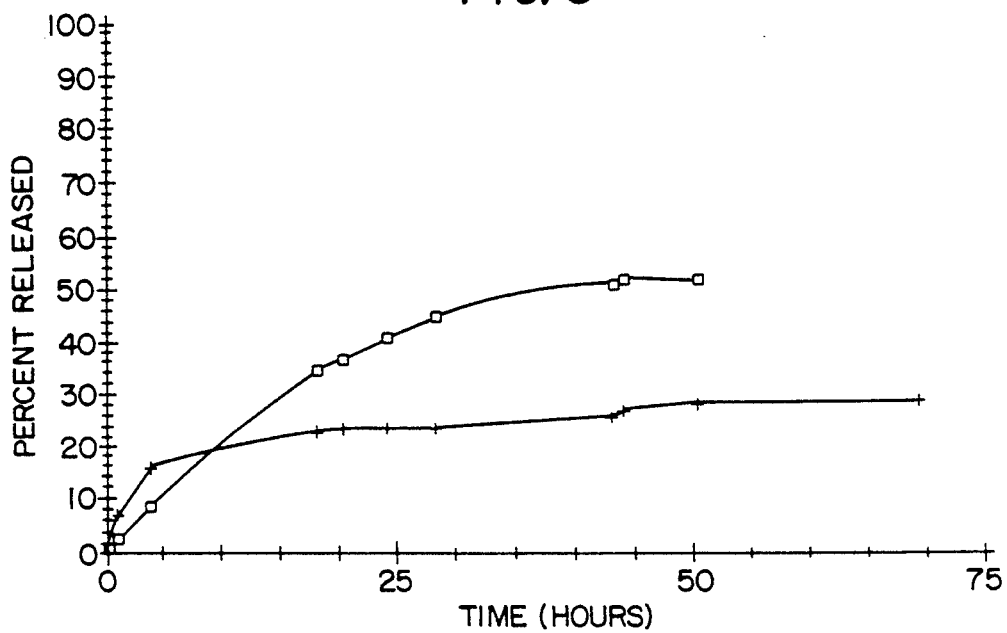
Figure 4:
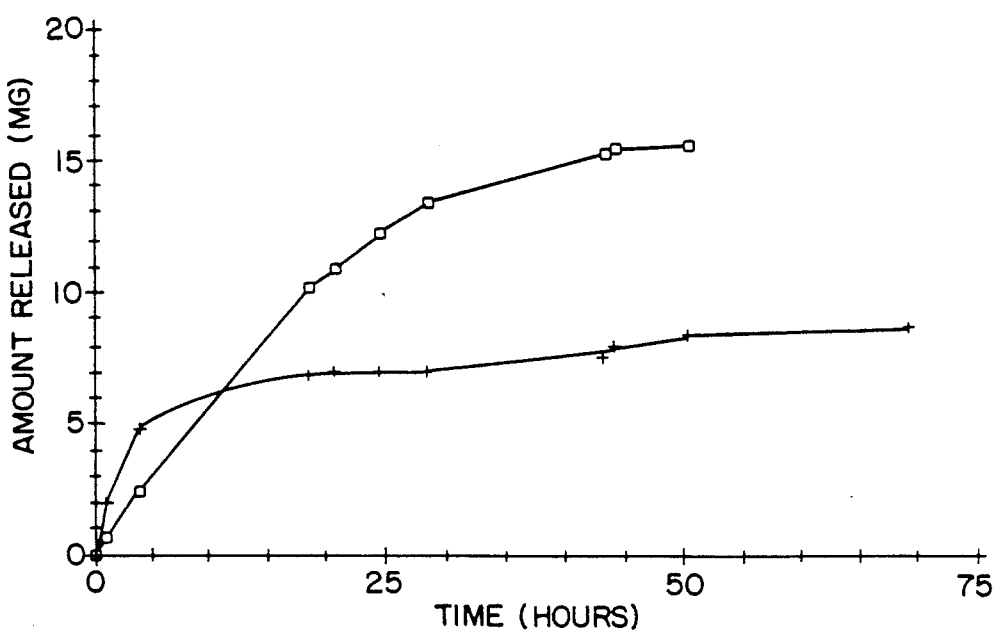
Figure 5:
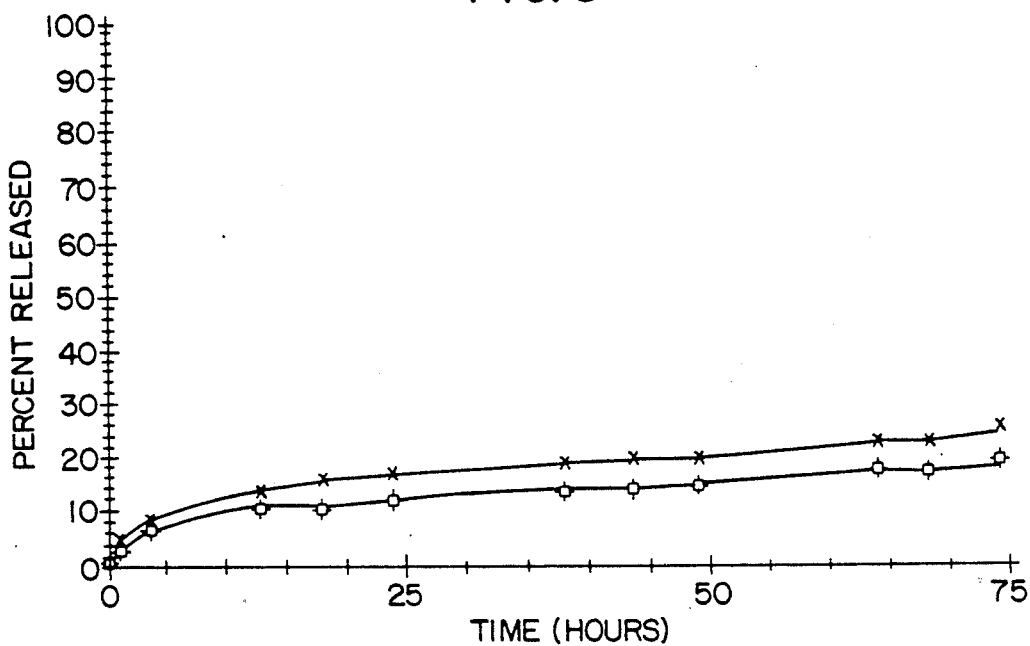

Sodium alginate, a water-soluble gum, was added to the polyaphron in an amount of 20 gm/liter to modify the release rate. These results are illustrated in FIGS. 3 and 4. The release rate of the scopolamine from the polyaphron is shown in a curve plotted by the squares and the alginate thickened polyaphron release rate is shown in the curve plotted with the pluses.

Figure 6:
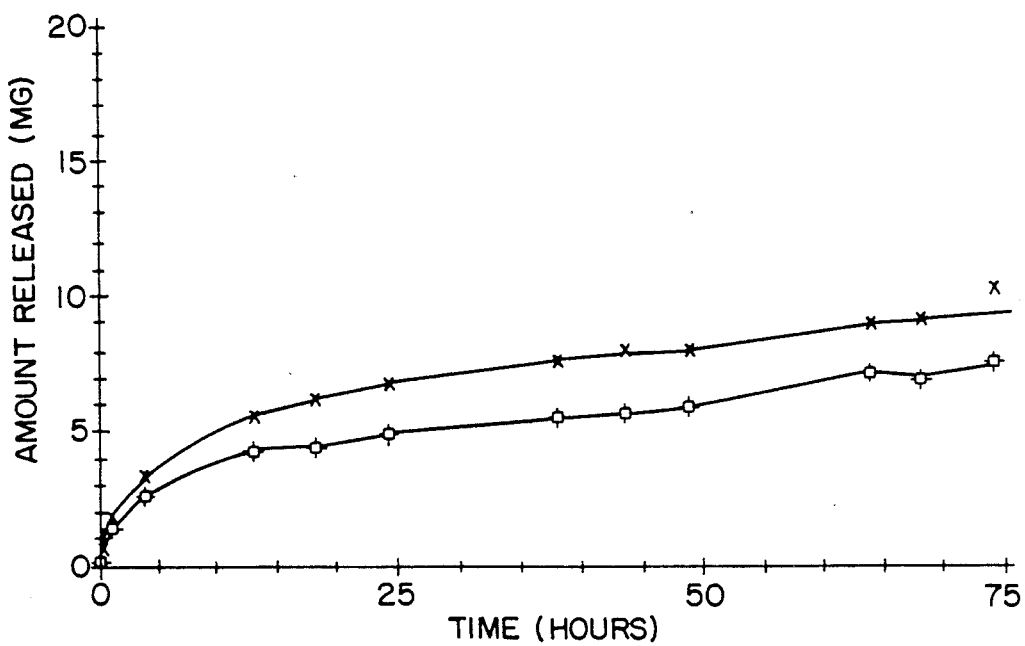

Other thickeners to control the release rate involved the addition of sodium carboxymethyl cellulose added in an amount of 20 gm/liter and identified in FIGS 6 and 7. The curve plotted with X's corresponds to the sodium carboxymethyl cellulose and the polyvinylacetate thickened polyaphron curve is plotted by the diamonds.

Although described with specific reference to certain oils and water and the addition of certain specific thickeners to control the release rate, the release rate can also be controlled by polymerization of either phase, such as by the addition of monomers to the oil and water phase to obtain polymerization at the interface for release control. Further, the polymerization concept is applicable in either phase in order to establish a matrix for precise control of delivery rates. Together with the possibility of polymerization, other surface active agents suitable for the particular continuous and dispersed phases may be used.

More particularly to enhance the flexibility of the Polyaphron in addition to the use of surface active agents per se the Aphron and the release rate of the substance.

Where the continuous phase is aqueous, soluble polymers such as alginates, zooglan, polyvinylchloride, polyhydroxyethyl methacrylate, and starches may be used. Water soluble monomers may also be added such as acrylates, for in situ polymerization.

Where the corresponding disperse phase is immiscible with water, such as in oil, oil soluable polymers such as polyacrylates, polystryenes, and polysodium styrene sulfonates may be used for control of drug release and dimensional stability. Oil soluble monomers such as styrenes, sodium styrene sulfonate and acrylates may be used for in situ polymerization.

The polymer-monomers may be used alone or in combination in a phase. One or both phases may use the polymers and monomers alone or in combination.

In a further variation of the invention interfacial polymerization may be provided for between the phases. For example, in an aqueous-nonaqueous aphron, such as where the nonaqueous phase is oil, the aqueous phase can contain an oil insoluble monomer such as a diamine. The nonaqueous phase can contain a aqueous monomer such as diacid chloride. The interfacial polymerization can control the release rate of the substance.

Having described the invention, what we now claim is:

1. A method for transferring a substance into a medium which includes:
    partitioning a polyaphron against the medium to define an interface, the polyaphron having at least one fluid continuous phase and a liquid disperse phase immiscible with the continuous phase, the polyaphron in fluid transfer relationship with the medium, the disperse phase carrying the substance therein and moving through the continuous phase in the direction of the medium and proceeding until coming into contact with the medium at the interface; and
    engaging subsequently in substance transfer relationship with the medium whereby the substance is then transferred into the medium from the disperse phase, the disperse phase being substantially in the form of droplets having a mean diameter size between $1\mu m-1$ mm.

2. The method of claim 1 wherein the polyaphron is a gel.

3. The method of claim 2 wherein the continuous phase includes a monomer insoluble with the disperse phase, and the disperse phase includes a monomer insoluble with the continuous phase, said monomers adapted for interfacial polymerization.

4. The method of claim 3 wherein the monomer in the continuous phase is a diamine and the monomer in the disperse phase is a diacid chloride.

5. The method of claim 1 wherein the liquid of the continuous phase is aqueous and the liquid of the disperse phase is selected from the group consisting of kerosene, alkanes, mineral oils and vegetable oils.

6. The method of claim 5 wherein the continuous phase includes a water soluble polymer.

7. The method of claim 6 wherein the water soluble polymer is selected from the group consisting of aliginates, xanthan, zooglan, polyhydroxyethyl methacrylate, starches and polyvinyl chloride.

8. The method of claim 7 wherein the continuous phase includes a water soluble monomer.

9. The method of claim 8 wherein the monomer is an acrylate.

10. The method of claim 1 wherein the disperse phase is a water immiscible fluid which includes a soluble polymer.

11. The method of claim 10 wherein the polymer is selected from the group consisting of polyacrylates and polystyrenes.

12. The method of claim 10 wherein the disperse phase includes a monomer.

13. The method of claim 12 wherein the monomer is selected from the group consisting of styrene, sodium styrene sulfonate, and acrylics.

14. The method of claim 1 wherein the continuous phase is aqueous.

15. The method of claim 1 wherein said substance is scopolamine.

* * * * *